United States Patent [19]

Sturm et al.

[11] Patent Number: 4,696,922
[45] Date of Patent: Sep. 29, 1987

[54] 5-AZOLYLACETOXYMILBEMYCINS AS ECTO- AND ENDOPARASITES

[75] Inventors: Elmar Sturm; Peter Maienfisch, both of Aesch, Switzerland

[73] Assignee: Ciba-Geigy Corporation, Ardsley, N.Y.

[21] Appl. No.: 799,373

[22] Filed: Nov. 18, 1985

[30] Foreign Application Priority Data

Nov. 26, 1984 [CH] Switzerland ............... 5631/84

[51] Int. Cl.$^4$ .................................. C07D 249/08
[52] U.S. Cl. ............................ 514/185; 514/382; 514/383; 514/359; 514/397; 514/407; 548/262; 548/253; 548/255; 548/336; 548/374; 548/101; 549/264
[58] Field of Search ............... 549/264, 265; 548/262, 548/253, 255, 336, 374, 101; 514/359, 382, 397, 383, 407, 185

[56] References Cited

FOREIGN PATENT DOCUMENTS

| 0139081 | 3/1982 | Japan | 549/264 |
| 0139079 | 8/1982 | Japan | 549/264 |
| 0016894 | 1/1984 | Japan | 549/264 |
| 0020284 | 2/1984 | Japan | 549/264 |

OTHER PUBLICATIONS

Tetrahedron Letters, 24, p. 5333, by H. Mrozik, (1983).

Primary Examiner—Glennon H. Hollrah
Assistant Examiner—Dara L. Dinner
Attorney, Agent, or Firm—Edward McC. Roberts; Meredith C. Findlay

[57] ABSTRACT

The present invention relates to milbemycin derivatives of the formula I

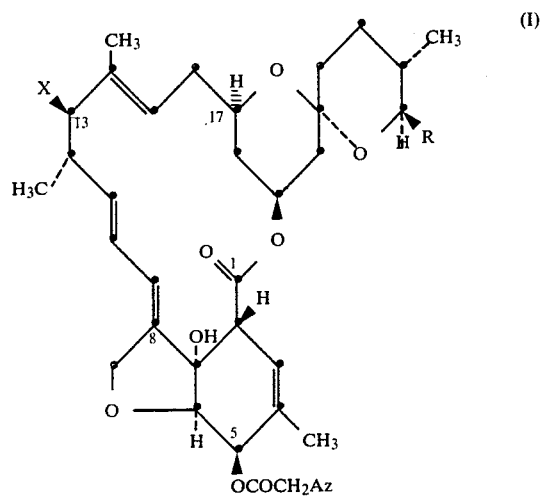

wherein X is hydrogen or $\beta$-halogen, R is methyl, ethyl, isopropyl or sec-butyl and Az is a 5 membered heterocyclic aromatic ring which contains 2–4 nitrogen atoms and is attached in the 1-position and which is unsubstituted or substituted by one or two $C_1$–$C_6$alkyl groups. These compounds, and the acid addition salts and metal complexes thereof, are effective pesticides for controlling endo-and ectoparasites, especially for controlling neamatodes which are parasites of animals. The may be obtained by appropriate esterification in 5-position of milbemycin derivatives. The selective $\beta$-halogenation of 14,15-epoxymilbemycin derivatives can be effected via the intermediate $\Delta^{13,14}$-15-hydroxymilbemycins with appropriate halogenating agents.

16 Claims, No Drawings

5-AZOLYLACETOXYMILBEMYCINS AS ECTO- AND ENDOPARASITES

The present invention relates to 5-azolylacetoxymilbemycin derivatives of formula I below and to the salts and metal complexes thereof, to the preparation of these compounds and to the use thereof for controlling pests such as ecto- and endoparasites. The invention further relates to pesticidal compositions which contain at least one of these compounds as active ingredient.

The compounds of the present invention are characterised by the formula I

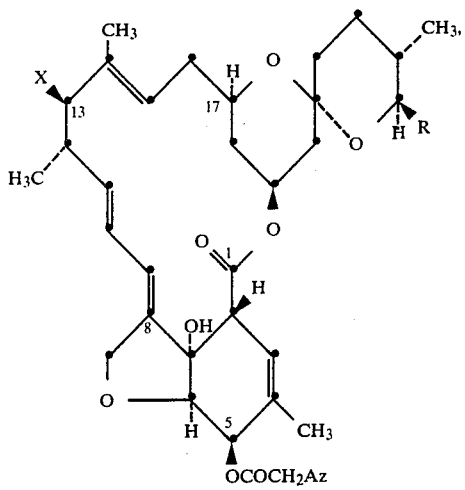

wherein X is hydrogen or β-halogen, R is methyl, ethyl, isopropyl or sec-butyl and Az is a 5 membered heterocyclic aromatic ring which contains 2–4 nitrogen atoms and is attached in the 1-position and which is unsubstituted or substituted by one or two $C_1$–$C_6$alkyl groups.

Examples of the substituent Az are: imidazole, pyrazole, 1,2,3-triazole, 1,2,4-triazole, 1,3,4-triazole or tetrazole, as well as azoles which are substituted by one or two $C_1$–$C_6$alkyl groups, e.g. 2-ethyl-4-methylimidazole, 2-isopropylimidazole, methylimidazole, 3,5-dimethyltriazole, ethyltriazole, 3,4-diethyltriazole and the like.

Halogen denotes fluorine, chlorine, bromine or iodine.

Salts of compounds of formula I are obtained with inorganic or organic acids. Suitable salt-forming acids are for example: hydrochloric acid, hydrobromic acid, sulfuric acid, nitric acid, phosphoric acid, methanesulfonic acid, p-toluenesulfonic acid, acetic acid, oxalic acid, tartaric acid, citric acid, ascorbic acid, sorbic acid, trimethylacetic acid, benzoic acid, salicylic acid, succinic acid and maleic acid.

Metal complexing agents are in particular cations of metals of auxiliary groups I and II or IV or VIII of the Periodic Table, e.g. copper, zinc, manganese, chromium, iron, nickel, cobalt and molybdenum.

The above recitations imply no restriction. Other physiologically tolerable salts and complex agents are known to the skilled person.

Within the scope of formula I, clear preference is given to those milbemycin derivatives wherein R is isopropyl and X and Az have the given meanings.

Important compounds are those of formula I, wherein X is hydrogen or chlorine, R is ethyl or isopropyl, and Az is 1,2,4-triazol-1-yl.

A particularly preferred compound is 5-O-(1,2,4-triazol-1'-yl)acetyl-13-β-chloromilbemycin D, and the salts and metal complexes thereof, especially its complexes with copper, zinc, manganese, chromium, iron, nickel, cobalt or molybdenum.

The starting materials of formula II, wherein X is hydrogen, are the known milbemycins

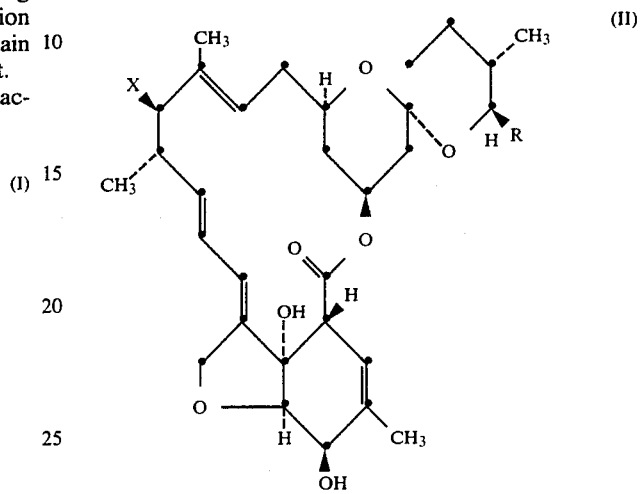

$R_2$=$CH_3$; milbemycin $A_3$ from U.S. Pat. No. 3,950,360;
$R_2$=$C_2H_5$; milbemycin $A_4$ from U.S. Pat. No. 3,950,360;
$R_2$=iso$C_3H_7$; milbemycin D from U.S. Pat. No. 4,346,171;
$R_2$=sec-$C_4H_9$; 13-deoxy-22,23-dihydro-C-076-Bla-aglycon, or 13-deoxy-22,23-dihydro-avermectin-Bla-aglycon from U.S. Pat. No. 4,173,571.

Throughout this specification, compounds wherein R is sec-butyl shall also be considered as belonging to the category of milbemycin derivatives, although they are derived from avermectin derivatives according to conventional classification. Avermectin aglycons (carrying an OH group in position 13) can, however, be converted into milbemycin homologs in accordance with U.S. Pat. No. 4,173,571.

Starting compounds of formula II, in which R and X are as defined above, are converted into the compounds of formula I in accordance with reaction scheme A

A:

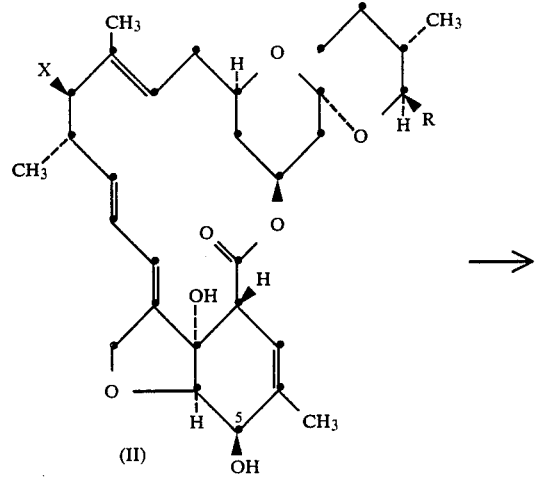

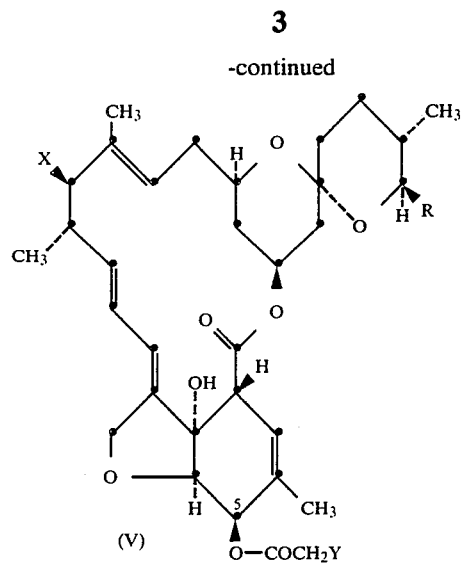

(V)

by converting the milbemycin derivative II at the 5-OH group into a compound of formula V by esterification with a substituted acetic acid $$Y-CH_2-CO-Z$$

Suitable acetic acid derivatives are derivatives capable of acetylation such as appropriately substituted acetyl halides or acetic anhydrides or the substituted acetic acid itself, all of which introduce the radical Y—CH$_2$—CO— in the 5-position. Thus Z is halogen, preferably chlorine or bromine, —OH or the half oxygen function in the acid anhydride. Y is halogen, preferably chlorine, bromine or iodine, or azido or another leaving group which may be readily replaced by nucleophilic exchange, such as the mesyl or tosyl group.

Preferred acetylating agents are chloroacetyl chloride, bromoacetyl chloride, azidoacetyl chloride, chloroacetic anhydride, 2-mesylacetyl chloride. The reaction is preferably carried out in an inert solvent that does not contain OH groups and in the presence of a base, e.g. pyridine, lutidine, collidine, trialkylamine, N-dialkylaniline, or a bicyclic non-nucleophilic base such as diazabicyclooctane (DABCO).

The Y-substituted 5-O-acetyl derivative of formula V is then reacted with an azole, preferably in the presence of a base, to give the final product of formula I. A suitable base is either the azole itself, used in excess, or a tertiary amine such as triethylamine, pyridine, DABCO or the like. These reactions proceed particularly smoothly in aprotic polar solvents such as dimethylsulfoxide, dimethylformamide, dimethylacetamide and the like.

In accordance with scheme B, the compounds of formula I may be prepared by a shortened process variant by reacting the milbemycin derivative II direct with a 2-azolylacetic acid or a derivative thereof:

B:

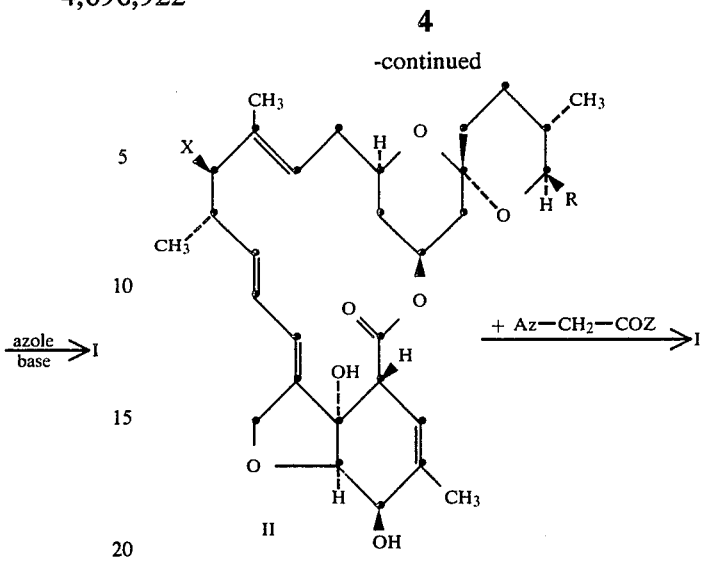

wherein Z is halogen, preferably chlorine or bromine, OH, or the half oxygen function in the anhydride (Az—CH$_2$—CO)$_2$O.

If the acid halides are used, the reaction is conveniently carried out in the presence of a tertiary organic base such as one of those cited above or in the presence of an inorganic base such as NaHCO$_3$ or K$_2$HPO$_4$ or Mg(OH)$_2$. The esterification with azolylacetic anhydride can be carried out without any special auxiliaries. To speed up the reaction, azolylacetic acid itself is employed and the reaction is carried out in the presence of condensing agents, for example dicyclohexylcarbodiimide and pyridine or a dialkylazodicarboxylate and triphenylphosphine.

Examples of such acetic acid derivatives are:

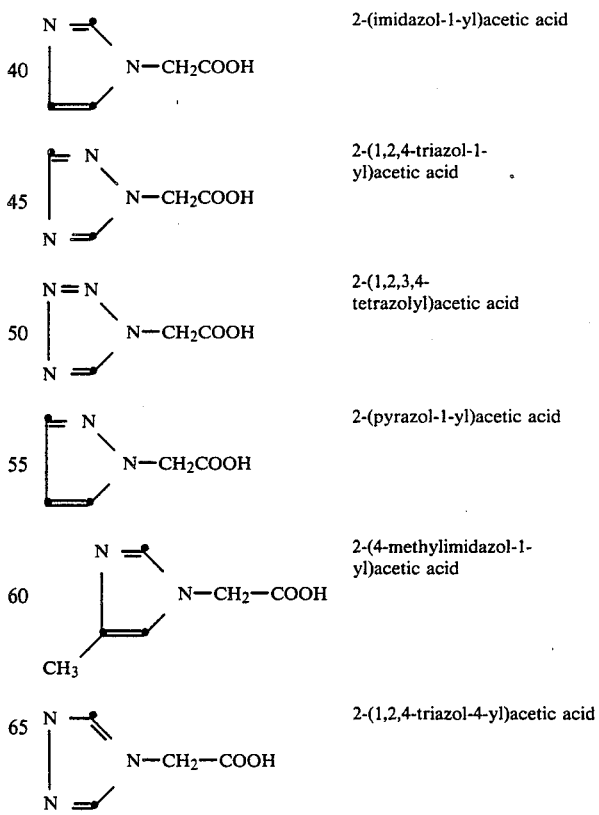

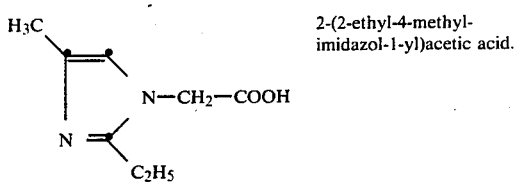

2-(2-ethyl-4-methyl-imidazol-1-yl)acetic acid.

The above exemplification implies no restriction.

As is evident, the above described reaction A is merely a division of reaction B into two partial steps.

Starting compounds of formula II, wherein X is a β-halogen atom, can be obtained from compounds of formula II, wherein X is hydrogen. This is accomplished by first rearranging the epoxide III,

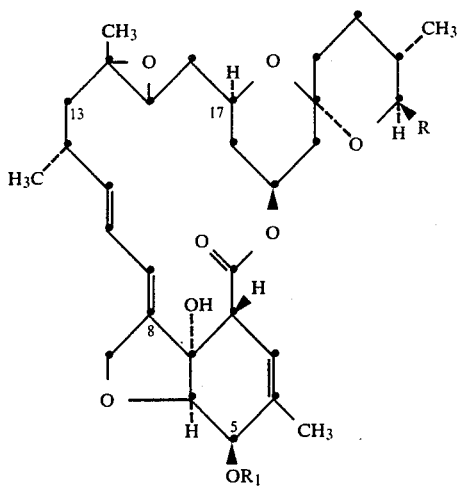

which is readily obtainable from milbemycin derivatives of formula II by conventional peroxide oxidation, and wherein $R_1$ is a hydrogen atom or a substituted silyl protective group such as dimethyl tert-butylsilyl, to give the $\Delta^{13,14}$-allyl alcohol of formula IV

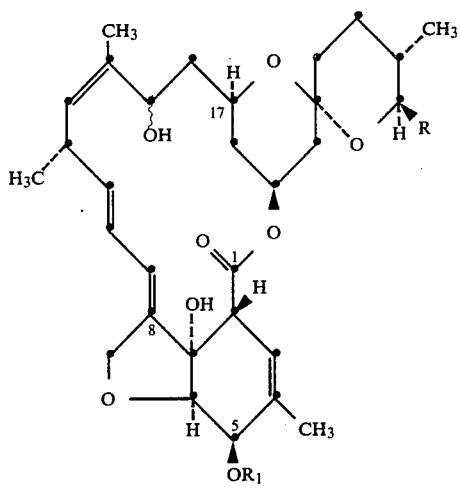

with a complex reagent $[HN_3]_m/[Al(ethyl)_3]_n$ described in more detail below.

The epoxide ring opening is conveniently carried out in an inert gas, e.g. nitrogen or argon.

The allyl alcohol IV, in which $R_1$ is preferably a silyl group which is substituted by aliphatic groups, is then converted, in characteristic and stereo-selective manner, into the 13β-halomilbemycin derivative of formula II (X=halogen) with a suitable halogenating agent on the general principle of an allylic rearrangement. For example, diethylaminosulfur trifluoride is used for the 13β-fluorination, thionyl chloride for the 13β-chlorination, phosphorus tribromide for the 13β-bromination and elemental iodine for the 13β-iodation, in combination with triphenylphosphine and imidazole.

The subsequent removal of the silyl radicals $R_1$ in the 5-position is effected by selective mild hydrolysis ($\rightarrow R_1 = H$) which is known to the skilled person, e.g. by saponification with an aromatic sulfonic acid.

The complex reagent cited above as suitable for the epoxide ring opening has the approximate formula $[HN_3]_m/[Al(ethyl)_3]_n$, wherein m and n are each independently of the other 1 or 2 or a value between 1 and 2, and is prepared in an inert solvent from the individual components $HN_3$ and $Al(C_2H_5)_3$ in the temperature range from $-30°$ to $+10°$ C. It is stable for a time at temperatures below zero. For the sake of simplicity, the reagent will hereinafter be referred to as $HN_3/Et_3Al$ or $HN_3/Al(C_2H_5)_3$. Any epoxy compound reacts in the presence of this reagent with opening of the oxirane ring and accompanied by simultaneous formation of a 1-hydroxy-2-azido compound and a substituted allyl alcohol (=1-hydroxy-$\Delta^{2,3}$ compound).

Hydrazoic acid $HN_3$ can also be converted, in statu nascendi, into the $[HN_3]_m/[Al(Et_3)_3]_n$ complex by suspending sodium azide in the dry solvent or mixture of solvents employed and generating therefrom $HN_3$ in the solution with a strong acid, e.g. $H_2SO_4$ (preferably oleum, in order to ensure absolutely dry reaction conditions). $Al(Et)_3$ should be already present in the solution or be added shortly afterwards. The epoxy compound to be reacted may also already be present or added to the solution at a suitable time.

The epoxidation of milbemycins of formula II (X=H) to compounds of formula III is carried out in a solvent phase in the temperature range from $-10°$ to $+20°$ C., preferably from $-5°$ to $+5°$ C.

Peracids such as peracetic acid, trifluoroperacetic acid, perbenzoic acid, chloroperbenzoic acid and others are suitable for the epoxidation.

The novel esters of formula V employed as intermediates, wherein R and X are as defined for formula I, likewise constitute an object of the invention. Esters of formula V are themselves useful compounds for controlling pests (e.g. endoparasites, ectoparasites and insects), as described in more detail below. Compounds meriting particular attention are the 5-O-chloroacetyl esters and 5-O-azidoacetyl esters of the milbemycin derivatives of formula V, which have outstanding anthelmintic and ectoparasiticidal properties.

The compounds of formula I are most suitable for controlling pests of animals and plants, including ectoparasites and endoparasites of animals. These last mentioned pests comprise those of the order Acarina, in particular pests of the families Ixodidae, Dermanyssidae, Sarcoptidae, Psoroptidae; of the orders Mallophaga, Siphonoptera, Anoptera (e.g. family of the Haematopinidae); and of the order Diptera, in particular pests of the families Muscidae, Calliphoridae, Oestrididae, Tabanidae, Hippoboscidae, and Gastrophilidae.

The compound of formula I can also be used against hygiene pests, especially of the order Diptera (families Sarcophigiae, Anophilidae and Culicidae); of the order Orthoptera (e.g. family of the Blattidae), and of the order Hymenoptera (e.g. family of the Formicidae).

The compounds of formula I also have a lasting action against mites and insects which are parasites of plants. When used to control spider mites of the order Acarina, they are effective against eggs, nymphs and adults of Tetranychidae (Tetranychus spp. and Panonychus spp.). They also have excellent activity against sucking insects of the order Homoptera, in particular against pests of the families Aphididae, Delphacidae, Cicadellidae, Psyllidae, Loccidae, Diaspididae and Eriophyidae (e.g. the rust mite on citrus fruit); of the orders Hemiptera, Heteroptera and Thysanoptera; and against plant-destructive insects of the orders Lepidoptera, Coleoptera, Diptera and Orthoptera.

The compounds of formula I are also suitable for use as soil insecticide against pests in the soil.

The compounds of formula I are therefore effective against all development stages of sucking and eating insects in crops such as cereals, cotton, rice, maize, soybeans, potatoes, vegetables, fruit, tobacco, hops, citrus fruit, avocados and others.

The compounds of formula are also effective against plant nematodes of the species Meloidogyne, Heterodera, Pratylenchus, Ditylenchus, Radopholus, Rhizoglyphus and others.

Furthermore, the compounds of formula I act against helminths, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Cappillaria, Heterakis, Toxocara, Ascaridia, Oxyuris, Ancylostoma, Uncinaria, Toxascaris and Parascaris. The particular advantage of the compounds of formula I is their activity against those parasites which are resistant to benzimidazole-based endoparasiticides.

Certain species of the genera Nematodirus, Cooperia and Oesophagostomum attack the intestinal tract of the host animal, whereas others of the species Haemonchus and Ostertagia parasiticise in the stomach and those of the species Dictyocaulus in the lung tissue. Parasites of the families Filariidae and Setariidae are found in internal cell tissue and internal organs, e.g. in the heart, blood vessels, lymph vessels and in subcutaneous tissue. The compound of formula I are very effective against these parasites.

The compounds of formula I are also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compound of this invention is also effective against parasites of the species Wucheraria, Brugia, Onchocera and Loa of the family of the Filariidae which occur in the blood, in tissue and various organs, and, in addition, against Dracunculus and parasites of the species Strongyloides and Trichinella which infest in particular the gastrointestinal tract.

The compounds of formula I are used in unmodified form or, preferably, together with the adjuvants conventionally employed in the art of formulation, and is therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 50 mg/kg of body weight, and are applied to enclosed crop areas, to pens, livestock buildings or other buildings in amounts of 10 g to 1000 g per hectare.

The formulations, i.e. the compositions or preparations containing the compounds (active ingredient) of formula I are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

The surfactants customarily employed in the art of formulation are described e.g. in "McCutcheon's Detergents and Emulsifiers Annual", MC Publishing Corp. Ridgewood, N.J., 1982.

The pesticidal compositions usually contain 0.01 to 95%, preferably 0.1 to 80%, of a compound of the formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1–10,000 ppm.

Accordingly, the present invention further relates to pesticidal compositions which contain, as at least one active ingredient, a compound of formula I, together with conventional carriers and/or diluents.

The compositions may also contain further ingredients, such as stabilisers, antifoams, viscosity regulators, binders, tackifiers as well as fertilisers or other active ingredients for obtaining special effects.

PREPARATORY EXAMPLES (α) Preparation of intermediates of formulae III and IV

1. Preparation of anhydrous $HN_3$ 1.1 In benzene: Preparation is carried out in accordance with the procedure described by H. Wolf, Org. Reactions 3, 307 (1946). The solution of $HN_3$ in benzene so obtained is dried twice over anhydrous $Na_2SO_4$ (heated for 30 min. over a flame and cooled in an exsiccator) and filtered through cotton wool at 0° C.→5° C. The solution is kept at 4° C. in a refrigerator.

1.2 In ether: Preparation is effected as in 1.1 except that the reaction temperature is kept at −20° C. to −10° C. during the addition of sulfuric acid. When the addition of $H_2SO_4$ is complete, the reaction mixture is warmed to −5° C.

2. Preparation of 14,15-epoxymilbemycin D (formula III)

While cooling with ice, a solution of 170 mg of chloroperbenzoic acid in 5 ml of dichloromethane is added to a solution of 550 mg of milbemycin D in 5 ml of dichloromethane. After stirring for 1 hour at 0° to 5° C., another 170 mg of the oxidising agent are added and stirring is continued for 30 minutes. When the reaction is complete, the solution is poured into an ice-cooled solution of sodium sulfite and extracted with ethyl acetate. The combined extracts are washed once with water, dried, and concentrated by evaporation in vacuo. The crude product is purified by chromatography through a column of silica gel (elution with a 20:15 mixture of n-hexane and ethyl acetate), affording 450 mg of amorphous, white 14,15-epoxymilbemycin D.

3. Preparation of 15-hydroxy-$\Delta^{13,14}$-milbemycin D (formula IV)

8.4 ml (0.41 g; 9.53 mmol) of a 6.96% solution of $HN_3$ in diethyl ether are added at −20° C. to a solution of 2.1 ml (1.75 g; 15.3 mmol) of triethyl aluminium in 8.5 ml of absolute diethyl ether. The reaction mixture is then added at −10° C. to 1.8 g (3.15 mmol) of 14,15-epoxymilbemycin D (in substance). The ensuing reaction is strongly exothermic. After 1 hour at room temperature, 4 ml of absolute ether are added and the gelatinous reaction mixture is vigorously stirred. After 4 hours the reaction mixture is worked up as described in Example 2. Chromatography through 70 g of silica gel (elution with a 10:1 mixture of $CH_2Cl_2$ and acetone) affords 200 mg (10%) of 14-azido-15-hydroxymilbemycin D and 820 mg (45%) of 15-hydroxy-$\Delta^{13,14}$-milbemycin D; m.p. 151°–153° C. (recrystallisation from methanol).

4. Preparation of 5-O-tert-butyldimethylsilyl-14,15-epoxymilbemycin D (formula III)

A solution of 2.21 g (3.86 mmol) of 14,15-epoxymilbemycin D, 757 mg (5.02 mmol) of tert-butyldimethylchlorosilane and 342 mg (5.02 mmol) of imidazole in 4 ml of dimethylformamide is stirred for 90 minutes at room temperature. Then 80 ml of diethyl ether are added and the mixture is filtered through 20 g of silica gel and the filtrate is concentrated, affording 2.65 g (100%) of 5-O-tert-butyldimethylsilyl-14,15-epoxymilbemycin D.

$^1$H-NMR (300 MHz. solvent $CDCl_3$. δ values based on $Si(CH_3)_4$=TMS). 0.12 ppm (s) $(CH_3)_2Si$—O—; 0.92 ppm (s) $(t-C_4H_9)Si$—O—; 1.23 ppm (broad s) $(C_{14}CH_3$, i.e. signal of the $CH_3$ group in the 14-position); 2.56 ppm (d; J=9) ($C_{15}H$, i.e. signal of the protons in the 15-position).

Following the same procedure, the corresponding 5-O-trimethylsilyl-14,15-epoxymilbemycin D (m.p. 92°–97° C.) can be prepared by reaction with trimethylsilyl trifluoromethanesulfonate.

5. Preparation of 5-O-tert-butyldimethylsilyl-15-hydroxy-$\Delta^{13,14}$-milbemycin D (formula IV)

A solution of the $HN_3/Et_3Al$ complex reagent (prepared from a solution of 4.97 ml of triethyl aluminium in 7 ml of absolute tetrahydrofuran and 9.15 ml of a 2.39 molar solution of $HN_3$ (21.9 mmol) in absolute diethyl ether) is added, under argon, to a solution of 5.0 g (7.29 mmol) of 5-O-tert-butyldimethylsilyl-14,15-epoxymilbemycin D in about 20 ml of absolute tetrahydrofuran, and the miture is heated under reflux for 16 hours. Then 250 ml of ether, 2 ml of methanol, and finally a mixture of 10 g of $Na_2SO_4.10H_2O$ and 10 g of celite are added at room temperature. The mixture is filtered and the filtrate is concentrated and chromatography of the crude product through 160 g silica gel (elution with 0–30% of ethyl acetate in hexane) affords 2.37 g (47%) of 5-O-tert-butyldiethylsilyl-15-hydroxy-$\Delta^{13,14}$-milbemycin D.

$^1$H-NMR (300 MHZ, $CDCl_3$): 1.59 (d; J=1) ($C_{14}CH_3$); 4.06 (dd; $J_1$=11; $J_2$=4) ($C_{15}H$); 5.15 (d; J=8) ($C_{13}H$).

In addition, 109 mg (2%) of 13β-azido-5-O-tert-butyldimethylsilylmilbemycin D are obtained.

6. Preparation of 14,15-epoxymilbemycin $A_4$ (formula III) ($R_2$=$C_2H_5$)

A solution of 2.43 g (14.08 mmol) of m-chloroperbenzoic acid in 70 ml of dichloromethane is added dropwise at room temperature to a solution of 5.7 g (10.5 mmol) of milbemycin $A_4$ in 140 ml of dichloromethane and 120 ml of a 0.5 molar solution of $NaHCO_3$. The mixture is vigorously stirred for 1 hour at room temperature and then diluted with 300 ml of dichloromethane. The organic phase is washed with an aqueous solution of $NaHCO_3$, dried over $Na_2SO_4$ and concentrated, affording 5.7 g of epoxide as crude product.

7. Preparation of 5-O-tert-butyldimethylsilyl-14,15-epoxymilbemycin $A_4$ (formula III)

5.7 g of 14,15-epoxy-milbemycin $A_4$ are dissolved in 10 ml of dry dimethylformamide. Then 0.63 g (9.16 mmol) of imidazole and 1.4 g (9.34 mmol) of tert-butyldimethylchlorosilane are added at room temperature. The mixture is stirred for 1 hour at room temperature and chromatographed through 150 g of silica gel (elution with a 4:1 mixture of hexane and ether), affording 2.84 g (40% of theory, based on milbemycin $A_4$) of the silylated epoxy derivative.

8. Preparation of 5-O-tert-butyldimethylsilyl-15-hydroxy-$\Delta^{13,14}$-milbemycin $A_4$ (formula IV)

The complex reagent $HN_3/Al(ethyl)_3$ is prepared as follows: To 2.8 ml (12.2 mmol) of $Al(C_2H_5)_3$ in 4 ml of absolute tetrahydrofuran are slowly added at about $-20°$ C., under argon, 5.28 ml (20.4 mmol) of an 10% solution of $HN_3$ in absolute diethyl ether. To this solution is added, under argon, a solution of 2.84 g (4.25 mmol) of the compound obtained in Example 7, and the mixture so obtained is heated for 4 hours under reflux. Then 500 ml of diethyl ether and 10 g of $Na_2SO_4.10H_2O$ and 10 g of celite are added at room temperature. The mixture is filtered and the filtrate is concentrated. Chromatography of the crude product through 100 g of silica gel (elution with a 7:2 mixture of hexane and diethyl ether) affords 1.72 g (60% of theory) of the title compound.

$^1$H-NMR (300 MHz, $CDCl_3$): 1.59 (broad s) ($C_{14}CH_3$); 4.05 (broad s) ($C_{15}H$); 5.15 (d; J=6) $C_{13}H$).

In addition, 0.1 g of 13$\beta$-azido-5-O-tert-butyldimethylsilylmilbemycin $A_4$ is obtained.

9. Preparation of 15-hydroxy-$\Delta^{13,14}$-milbemycin $A_4$ (formula IV)

Hydrolysis of 5 mg of the title compound of Example 8 with 1 ml of a 1% solution of p-toluenesulfonic acid in methanol and working up in diethyl ether with a 5% solution of sodium bicarbonate affords the title compound.

10. Preparation of 14,15-epoxymilbemycin $A_3$ (formula III) ($R_2=CH_3$)

In accordance with the procedure described in Example 2, reaction of 220 mg of milbemycin $A_3$ in 5 ml of dichloromethane and 320 mg of benzoperacid in 5 ml of dichloromethane at $-2°$ to $+5°$ C. over 1½ hours and purification through a column of silica gel affords 190 mg of 14,15-epoxymilbemycin $A_3$.

11. Preparation of 5-O-methyldiphenylsilyl-14,15-epoxymilbemycin $A_3$ (formula III)

In accordance with the procedure of Example 4, reaction of 190 mg of 14,15-epoxymilbemycin $A_3$ and 120 mg of diphenylmethylchlorosilane in the presence of imidazole affords 217 mg of the title compound.

12. Preparation of 5-O-methyldiphenylsilyl-15-hydroxy-$\Delta^{13,14}$-milbemycin $A_3$ (formula IV)

In accordance with the epoxy cleavage of Example 5, 203 g of the title compound are obtained from 210 g of 5-O-methyldiphenylsilyl-14,15-epoxymilbemycin $A_3$ in absolute diethyl ether using the complex reagent $HN_3/Et_3Al$ under argon, and subsequent purification.

$^1$H-NMR (300 MHz, $CDCl_3$): 1.58 (broad s) ($C_{14}CH_3$); 4.05 (broad s) ($C_{15}H$); 5.15 (d; J=6) ($C_{13}H$).

13. Preparation of 15-hydroxy-$\Delta^{13,14}$-milbemycin $A_3$ (formula IV)

In accordance with the procedure described in Example 2, the reagent $HN_3/Al(C_2H_5)_3$ is freshly prepared and added dropwise at $-10°$ C. to a solution of 830 mg (3.05 mmol) of 14,15-epoxymilbemycin $A_3$ in 7 ml of dry diethyl ether. After working up, 385 mg of 15-hydroxy-$\Delta^{13,14}$-milbemycin $A_3$ and 92 mg of 14-azido-15-hydroxymilbemycin $A_3$ are obtained.

14. Preparation of 13-deoxy-14,15-epoxy-22,23-dihydroavermectin-Bla-aglycon ($R_2$=sec-$C_4H_9$) (formula III)

In accordance with the procedure described in Example 6, 510 mg of the title compound are obtained from 520 mg of 13-deoxy-22,23-dihydroavermectin-Bla-aglycon [Tetrahydron Letters, Vol. 24, No. 48, pp. 5333–5336 (1983)] and 210 mg of m-chlorobenzoperacid in 20 ml of dichloromethane.

15. Preparation of 5-O-tert-butyldimethylsilyl-13-deoxy-14,15-epoxy-22,23-dihydroavermectin-Bla-aglycon (formula III)

In accordance with the procedure described in Example 7, 108 mg of the title compound are obtained from 220 mg of the title compound of Example 14 and 55 mg of tert-butyldimethyldichlorosilane in the presence of 25 mg of imidazole in 5 ml of dry dimethylformamide.

16. Preparation of 13-deoxy-15-hydroxy-$\Delta^{13,14}$-22,23-dihydroavermectin-Bla-aglycon (formula IV)

In accordance with the procedure described in Example 3, 112 mg of the title compound are obtained by reacting 220 mg of the title compound of Example 15 with the complex reagent consisting of 320 mg of $Al(C_2H_5)_3$ and 110 mg of a 6.96% solution of $HN_3$ in a total of 16 ml of dry diethyl ether. In addition, 61 mg of 13-deoxy-14-azido-15-hydroxy-22,23-dihydroavermectin-Bla-aglycon are obtained.

($\beta$) Preparation of compounds of formula (II) (X=halogen)

17. Preparation of 5-O-tert-butyldimethylsilyl-13$\beta$-fluoromilbemycin D and 13$\beta$-fluoromilbemycin D (formula I)

Under argon, a solution of 18.3 $\mu$l (24 mg; 0.15 mmol) of diethylaminosulfur trifluoride (DAST) in 0.15 ml of dry dichloromethane is added dropwise at $-60°$ C. to a solution of 103 mg (0.15 mmol) of 5-O-tert-butyldimethylsilyl-15-hydroxy-$\Delta^{13,14}$-milbemycin D in 1.5 ml of dichloromethane. After 10 minutes, the reaction mixture is worked up with a 5% aqueous solution of $NaHCO_3$ and with diethyl ether. The organic phase is dried over $MgSO_4$ and concentrated, affording 100 mg of 5-O-tert-butyldimethylsilyl-13$\beta$-fluoro-milbemycin D which is stirred in 2 ml of a 1% solution of p-toluenesulfonic acid in methanol for 1 hour at room temperature. The reaction mixture is worked up with a 5% aqueous solution of $NaHCO_3$ and by extraction with three 2 ml portions of diethyl ether. Chromatography of the crude product through 20 g of silica gel (elution with a 1:12 mixture of acetone and dichloromethane) affords 58 mg (67% of theory) of 13$\beta$-fluoromilbemycin D.

$^1$H-NMR (300 MHz; $CDCl_3$; TMS): 1.61 ppm (br. s) ($C_{14}CH_3$); 2.5–2.7 ppm (m) ($C_{12}H$); 4.40 ppm (dd; $J_1=48$; $J_2=10$) ($C_{13}H$).

Mass spectrum m/e: 574 (M+, 6% of $C_{33}H_{47}FO_7$), 446, 374, 332, 428, 151.

18. Preparation of 5-O-tert-butyldimethylsilyl-13β-fluoromilbemycin $A_4$ and 13β-fluoromilbemycin $A_4$ (formula I)

In accordance with the procedure described in Example 24, 183 mg of 5-O-tert-butyldimethylsilyl-13β-fluoromilbemycin $A_4$ are obtained from 202 mg of 5-O-tert-butyldimethylsilyl-15-hydroxy-$\Delta^{13,14}$-milbemycin $A_4$ and 36.2 μl of DAST. Subsequent desilylation with methanolic p-toluenesulfonic acid affords 114 mg of 13β-fluoromilbemycin $A_4$.

$^1$H-NMR (300 MHz; CDCl$_3$; TMS): 1.61 (s) ($C_{14}CH_3$); 4.42 (dd; $J_1=47$; $J_2=10$) ($C_{13}H$).

19. Preparation of 5-O-methyldiphenylsilyl-13β-fluoromilbemycin $A_3$ and —β-fluoromilbemycin $A_3$ (formula I)

In accordance with the procedure described in Example 24, 81 mg of 5-O-methyldiphenylsilyl-13β-fluoromilbemycin $A_3$ are obtained from 108 mg of 5-O-methyldiphenylsilyl-15-hydroxy-$\Delta^{13,14}$-milbemycin $A_3$ and 19.0 μl of DAST. Subsequent desilylation with methanolic p-toluenesulfonic acid in the 5-position affords 68 mg of 13β-fluoromilbemycin $A_3$.

20. Preparation of 5-O-tert-butyldimethylsilyl-13β-chloromilbemycin D and 13β-chloromilbemycin D (formula I)

Under argon and with ice/methanol cooling (circa $-10°$ C.), 8.5 μl (13.9 mg; 0.116 mmol) of thionyl chloride are added dropwise to a solution of 50 mg (0.073 mmol) of 5-O-tert-butyldimethylsilyl-15-hydroxy-$\Delta^{13,14}$-milbemycin D in 1.5 ml of dry dichloromethane. The reaction is promoted by the presence of 2 equivalents (0.146 mmol) of triethylamine. After 5 minutes, the mixture is extracted with a 5% aqueous solution of NaHCO$_3$ and then with diethyl ether. The organic phase is dried over MgSO$_4$ and concentrated. Chromatography of the crude product through a column of 20 g of silica gel (elution with a 1:20 mixture of ethyl acetate and hexane) affords 17 mg (30% of theory) of 5-O-tert-butyldimethylsilyl-13β-chloromilbemycin D.

$^1$H-NMR (300 MHz; CDCl$_3$; TMS): 0.93 (s) ($C_5$—O—SiC(CH$_3$)$_3$—); 0.13 (s) ($C_5$—OSi(CH$_3$)$_2$—); 2.45–2.65(m) ($C_{12}H$); 4.08 (d; J=11) ($C_{13}H$).

Treatment of the silylated compound with 1% p-toluenesulfonic acid in methanol for 1 hour affords, after treatment with a 5% aqueous solution of NHCO$_3$, extraction with diethyl ether and chromatography through silica gel (elution with a 2:3 mixture of ethyl acetate and hexane), 13β-chloromilbemycin D in quantitative yield.

$^1$H-NMR (300 MHz; CDCl$_3$; TMS): 1.67 (s) ($C_{14}CH_3$); 5.24 (d; J=11) ($C_{13}\alpha H$).

21. Preparation of 5-O-tert-butyldimethylsilyl-13β-bromomilbemycin D and 13β-bromomilbemycin D (formula I)

Under argon, 0.013 ml (36 mg; 0.133 mmol) of PBr$_3$ are added dropwise with stirring at $-10°$ C. to a solution of 182 mg (0.265 mmol) of 5-O-tert-butyldimethylsilyl-15-hydroxy-$\Delta^{13,14}$-milbemycin D in 5 ml of dry dichloromethane. After 5 minutes, 0.1 ml of methanol is added, the mixture is diluted with ether and the organic phase is washed with a 5% aqueous solution of NaHCO$_3$, dried over MgSO$_4$ and filtered through silica gel. Chromatography of the crude product though 20 g of silica gel (elution with a 1:4 mixture of ethyl acetate and hexane [100 ml] and then with a 2:3 mixture of ethyl acetate and hexane [250 ml]) affords 98 mg (49% of theory) of 5-O-tert-butyldimethylsilyl-13β-bromomilbemycin D and 50 mg (30% of theory) of 13β-bromomilbemycin D. Treatment of the tert-butyldimethylsilyl ether derivative with 2 ml of a 1% solution of p-toluenesulfonic acid in methanol (1 hour at room temperature) followed by working up in diethyl ether with a 5% aqueous solution of NaCHO$_3$ and chromatography through silica gel (elution with a 2:3 mixture of ethyl acetate and hexane) affords 13β-bromomilbemycin in quantitative yield.

$^1$H-NMR (300 MHz; CDCl$_3$; TMS): 1.68 (s) ($C_{14}CH_3$); 1.87 (s) ($C_4CH_3$); 4.30 (d; J=10.7)($C_{13}H$).

Mass spectrum m/e: 636, 634 (M+; $C_{33}H_{47}BrO_7$), 508, 506, 427, 209, 149, 41. 13β-Bromomilbemycin $A_4$ with mass spectrum m/e: 622, 620 is obtained in analogous manner.

22. Preparation of 5-O-tert-butyldimethylsilyl-13β-iodomilbemycin D and 13β-iodomilbemycin D (formula I)

Under argon, a solution of 526 mg (0.776 mmol) of 5-O-tert-butyldimethylsilyl-15-hydroxy-$\Delta^{13,14}$-milbemycin D, 439 mg (1.884 mmol) of triphenylphosphine, 128 mg (1.884 mmol) of imidazole and 292 mg (1.149 mmol) of iodine in 10 ml of dry dichloromethane is stirred for 20 minutes at room temperature. The mixture is diluted with diethyl ether, washed with a 5% aqueous solution of NaHCO$_3$ and the organic phase is dried over MgSO$_4$. Chromatography of the crude product through 75 g of silica gel (elution with a 1:12 mixture of ethyl acetate and hexane [500 ml]) affords 390 mg (64%) of 5-O-tert-butyldimethylsilyl-13β-iodomilbemycin D.

159 mg (0.20 ml) of this silylated compound are stirred in 2 ml of a 1% solution of p-toluenesulfonic acid in methanol for 1 hour at room temperature. The mixture is then worked up with a 5% aqueous solution of NaHCO$_3$ and with diethyl ether. Chromatography through a column of 20 g of silica gel (elution with a 2:3 mixture of ethyl acetate and hexane) affords 103 mg (76% of theory) of 13β-iodomilbemycin D.

$^1$H-NMR (300 MHz; CDCl$_3$; TMS): 1.64 (s) ($C_{14}CH_3$); 1.82 (s) ($C_4CH_3$) 4.52 (d; J=11.0) ($C_{13}H$).

23. Preparation of 5-O-tert-butyldimethylsilyl-13β-chloromilbemycin $A_4$ and 13β-chloromilbemycin $A_4$ (formula I)

Under argon, 0.026 ml (=42 mg; 0.354 mmol) of thionyl chloride is added dropwise with stirring at $-10°$ C. to a solution of 198 mg (0.295 mmol) of 5-O-tert-butyldimethylsilyl-15-hydroxy-$\Delta^{13,14}$-milbemycin $A_4$ and 0.082 ml (=60 mg; 0.589 mmol) of triethylamine in 5 ml of dry dichloromethane. After 5 minutes, 0.1 ml of methanol is added. The mixture is worked up with a 5% solution of NaHCO$_3$ and with diethyl ether (=ether). Chromatography through 20 g of silica gel (elution with a 1:19 mixture of ethyl acetate and hexane) affords 96 mg (47%) of 5-O-tert-butldimethylsilyl-13β-chloromilbemycin $A_4$.

This product is stirred in 2 ml of 1% solution of p-toluenesulfonic acid in methanol for 1 hour at room temperature. The mixture is then treated with a 5% aqueous solution of NaHCO$_3$. Chromatography through 20 g of silica gel (elution with a 2:3 mixture of ethyl acetate and hexane) affords 66 mg (82% of theory) of 13β-chloromilbemycin $A_4$.

$^1$H-NMR (250 MHz; CDCl$_3$; TMS): 1.67 (s) ($C_{14}CH_3$); 3.10 (t) (J=ca. 7 Hz) ($C_{25}H$); 5.24 (d) (J=ca. 11 Hz) ($C_{13}H$).

Mass spectrum m/e: 576 (M+, $C_{32}H_{45}O_7Cl$), 448, 442, 348, 279, 195, 167, 151.

24. Preparation of 5-O-methyldiphenylsilyl-13β-chloromilbemycin A$_3$ and 13β-chloromilbemycin A$_3$ (formula I)

In accordance with the procedure described in Example 13, 122 mg of 5-O-methyldiphenylsilyl-13β-chloromilbemycin A$_3$ are obtained from 194 mg of 5-O-methyldiphenylsilyl-15-hydroxy-Δ$^{13,14}$-milbemycin A$_3$ and 0.025 ml of SOCl$_2$. After subsequent removal of the silyl radical 83 mg of 13β-chloromilbemycin A$_3$ are obtained.

$^1$H-NMR (250 MHz; CDCl$_3$; TMS): 1.64 (s) (C$_{14}$CH$_3$); 1.87 (s) (C$_4$CH$_3$); 4.08 (d) (J=11 Hz) (C$_{13}$H).

25. Preparation of 5-O-tert-butyldimethylsilyl-13α-chloro-22,23-dihydroavermectin-Bla-aglycon and 13α-chloro-22,23-dihydroavermectin-Bla-aglycon (formula I)

Under argon, 0.041 ml (=67 mg; 0.561 mmol) of SOCl$_2$ are added dropwise with stirring at −10° C. to a solution of 327 mg (0.467 mmol) of 5-O-tert-butyldimethylsilyl-22,23-dihydroavermectin-Bla-aglycon and 0.130 ml (=95 mg; 0.934 mmol) of triethylamine in 10 ml of dry dichloromethane. After 5 minutes, 0.1 ml of methanol is added. The mixture is worked up with a 5% aqueous solution of NaHCO$_3$ and with ether. Chromatography of the crude product through 20 g of silica gel (elution with a 1:9 mixture of ethyl acetate and hexane) affords 117 mg (50% of theory) of 5-O-tert-butyldimethylsilyl-13α-chloro-22,23-dihydroavermectin-Bla-aglycon.

This product is desilylated with 2 ml of a 1% solution of p-toluenesulfonic acid in CH$_3$OH for 1 hour at room temperature with stirring. The mixture is then worked up with a 5% aqueous solution of NaHCO$_3$ and with ether. Chromatography through 20 g of silica gel (elution with a 2:3 mixture of ethyl acetate and hexane) affords 68 mg (69% of theory) of 13α-chloro-22,23-dihydroavermectin-Bla-aglycon.

$^1$H-NMR (300 MHz; CDCl$_3$; TMS): 1.63 (s) (C$_{14}$CH$_3$); 1.87 (s) (C$_4$CH$_3$); 4.39 (s) (W$_{\frac{1}{2}}$=6 Hz) (C$_{13}$H).

Mass spectrum m/e: 604 (M$^+$, C$_{34}$H$_{49}$O$_7$Cl), 476, 348, 223, 195, 151.

(γ) Preparation of compounds of formula V

26. Preparation of 5-O-chloroacetylmilbemycin D (=Z-1)

While cooling with ice (0°–5° C.), 168 mg of chloroacetyl chloride are slowly added dropwise with an injection syringe to a solution of 400 mg of milbemycin D in 10 ml of pyridine. The cloudy yellowish reaction solution is poured at 0° C. into 100 ml of ice-cold 1N aqueous hydrochloric acid and extracted with four 20 ml portions of diethyl ether (ether). The carefully washed and dried ether solution is concentrated in vacuo, affording an amorphous foamy product which is purified by chromatography through a column of silica gel (elution with a 98:2 mixture of methylene chloride/methanol), affording 410 mg of colourless amorphous final product.

$^1$H-NMR (300 MHz; CDCl; TMS=tetramethylsilane) 5.32 (s) (—CH$_2$—Cl), 3.25 (narrow multiplet) (C$_2$H; i.e. H-signal in position 2); mass spectrum m/e: 632 (M$^+$; C$_{35}$H$_{49}$ClO$_8$).

27. Preparation of 5-O-bromoacetylmilbemycin A$_4$ (=Z-2)

Following the procedure of Example 26, 5-O-bromoacetylmilbemycin A$_4$ is obtained as an amorphous solid from milbemycin A$_4$ (R=C$_2$H$_5$) and bromoacetyl bromide in pyridine.

28. Preparation of 5-O-iodoacetylmilbemycin D (=Z-3)

150 mg of 5-O-chloroacetylmilbemycin D and 50 mg of potassium are dissolved in 10 ml of acetone and the solution is stirred for 24 hours at room temperature. The reaction mixture is diluted with the 5-fold amount of water and then extracted with four 10 ml portions of diethyl ether. The crude product obtained from the ether solution is chromatographed through a column of silica gel (q.v. Example 26), affording 80 mg of pure product (m.p. 133°–137° C.).

29. Preparation of 5-O-azidoacetylmilbemycin D (=Z-4)

Following the procedure of Example 28, 92 mg of 5-O-azidoacetylmilbemycin D are obtained from 150 mg of 5-O-chloroacetylmilbemycin D and 35 mg of sodium azide (NaN$_3$).

30. Preparation of 5-O-chloroacetyl-13β-chloromilbemycin A$_4$ (=Z-10)

To a solution of 650 mg of 13β-chloromilbemycin A$_4$ in 6 ml of methylene chloride are added 0.90 ml of pyridine and then, at 0° C. over 30 minutes, 0.14 ml of chloroacetyl chloride. The reaction mixture is stirred for 2 hours at 0° C. and then poured into 100 ml of 0.2N HCl solution and extracted with three 50 ml portions of diethyl ether. The organic phases are combined, then washed with 100 ml of saturated NaCl solution, dried over MgSO$_4$ and filtered. The filtrate is concentrated and the crude product is chromatographed through a column of silica gel (elution with a 2:1 mixture of hexane/diethyl ether), affording 524 g of 5-O-chloroacetyl-13β-chloromilbemycin A$_4$.

$^1$H-NMR (250 MHz, CDCl$_3$): 3.06 (dt, J$_d$=3, J$_t$=9) (C$_{25}$H); 4.14 (d, J=13) (C$_{13}$H); 4.17 (s) (CH$_2$Cl).

The following intermediates of formula V can also be prepared in accordance with the foregoing Examples:
Nr.

Z5. 5-O-bromocetylmilbemycin A$_4$,
Z6. 5-O-bromoacetylmilbemycin D,
Z7. 5-O-chloroacetylmilbemycin A$_4$,
Z8. 5-O-chloroacetyl-13β-chloromilbemycin D,
Z9. 5-O-chloroacetyl-13β-fluoromilbemycin D,
Z10. 5-O-chloroacetyl-13β-chloromilbemycin A$_4$,
Z11. 5-O-chloroacetyl-13β-chloromilbemycin A$_3$,
Z12. 5-O-iodoacetyl-13β-chloromilbemycin D,
Z13. 5-O-chloroacetyl-13β-bromomilbemycin A$_4$,
Z14. 5-O-fluoroacetylmilbemycin D,
Z15. 5-O-methylsulfonyloxyacetylmilbemycin D,
Z16. 5-O-p-tosyloxyacetylmilbemycin D,
Z17. 5-O-azidoacetylmilbemycin A$_3$,
Z18. 5-O-azidoacetylmilbemycin A$_4$,
Z19. 5-O-ethylsulfonyloxyacetylmilbemycin A$_4$,
Z20. 5-O-chloroacetyl-13-deoxy-22,23-dihydroavermectin-Bla-aglycon,
Z21. 5-O-bromoacetyl-13-deoxy-22,23-dihydroavermectin-Bla-aglycon,
Z22. 5-O-azidoacetyl-13-deoxy-22,23-dihydroavermectin-Bla-aglycon,
Z23. 5-O-chloroacetyl-13-deoxy-13β-chloro-22,23-dihydroavermectin-Bla-aglycon,
Z24. 5-O-bromoacetyl-13-deoxy-13β-chloro-22,23-dihydroavermectin-Bla-aglycon,
Z25. 5-O-bromoacetyl-13β-chloromilbemycin D,
Z26. 5-O-bromoacetyl-13β-chloromilbemycin A$_4$,
Z27. 5-O-bromoacetyl-13β-chloromilbemycin A$_3$,
Z28. 5-O-fluoroacetyl-13β-chloromilbemycin A$_4$,
Z29. 5-O-fluoroacetyl-13β-chloromilbemycin D,
Z30. 5-O-azidoacetyl-13β-chloromilbemycin A$_4$, Z31. 5-O-azidoacetyl-13β-chloromilbemycin D,
Z32. 5-O-azidoacetyl-13-deoxy-13β-chloro-22,23-dihydroavermectin-B1a-aglycon,
Z33. 5-O-benzenesulfonyloxyacetyl-13β-chloromilbemycin A4,
Z34. 5-O-(p-tosyloxy)-acetyl-13β-chloromilbemycin D,
Z35. 5-O-chloroacetyl-13β-fluoromilbemycin A3,
Z36. 5-O-chloroacetyl-13β-fluoromilbemycin A4,
Z37. 5-O-chloroacetyl-13-deoxy-13β-fluoro-22,23-dihydroavermectin-B1a-aglycon,
Z38. 5-O-bromoacetyl-13β-fluoromilbemycin A4,
Z39. 5-O-bromoacetyl-13β-fluoromilbemycin D,
Z40. 5-O-bromoacetyl-13-deoxy-13β-fluoro-22,23-dihydroavermectin-B1a-aglycon,
Z41. 5-O-fluoroacetyl-13β-fluoromilbemycin A4,
Z42. 5-O-fluoroacetyl-13β-fluoromilbemycin D,
Z43. 5-O-iodoacetyl-13β-fluoromilbemycin D,
Z44. 5-O-azidoacetyl-13β-fluoromilbemycin A4,
Z45. 5-O-azidoacetyl-23β-fluoromilbemycin D,
Z46. 5-O-azidoacetyl-13-deoxy-13β-fluoro-22,23-dihydroavermectin-B1a-aglycon,
Z47. 5-O-chloroacetyl-13β-bromomilbemycin A3,
Z48. 5-O-chloroacetyl-13β-bromomilbemycin D,
Z49. 5-O-chloroacetyl-13-deoxy-13β-bromo-22,23-dihydroavermectin-B1a-aglycon,
Z50. 5-O-bromoacetyl-13β-bromomilbemycin A4,
Z51. 5-O-bromoacetyl-13β-bromomilbemycin D,
52. 5-O-bromoacetyl-13-deoxy-13β-bromo-22,23-dihydroavermectin-B1a-aglycon,
Z53. 5-O-fluoroacetyl-13β-bromomilbemycin A4,
Z54. 5-O-fluoroacetyl-13β-bromomilbemycin D,
Z55. 5-O-azidoacetyl-13β-bromomilbemycin D.

Preparation of compounds of formula I

31. Preparation of 5-O-(1,2,4-triazol-1'-yl)acetylmilbemycin D (compound 2.1)

150 mg of 5-O-chloroacetylmilbemycin D and 33 mg of 1,2,4-triazole are dissolved in 5 ml of dry dimethylformamide and the solution is stirred for 40 hours at a bath temperature of 120° C. under an atmosphere of argon. The dark reaction solution is diluted with ice water and extracted with three 3 ml portions of ether. The dark brown resin so obtained is chromatographed through a column of silica gel (elution with a 95:5 mixture of methylene/methanol). The main fraction gives 70 mg of a yellowish amorphous substance.

$^1$H-NMR (300 MHz, CDCl$_3$, TMS) (s) (—CH$_2$-triazol), 8.0 and 8.25 (2 s) (triazole ring protons), 3.26 (narrow multiplet) (C$_2$—H). mass spectrum m/e: 665 (M+, C$_{37}$H$_{51}$N$_3$O$_8$).

32. Preparation of 5-O-(4'-methylimidazol-1'-yl)acetylmilbemycin D and 5-O-(5'-methylimidazol-1'-yl)acetylmilbemycin D (compounds 2.2 and 2.3)

150 mg of 5-O-chloroacetylmilbemycin D and 37.7 mg of 4(5)-methylimidazole are stirred for 3 hours in 5 ml of dimethylformamide at a bath temperature of 100° C. Thin-layer chromatography confirms complete reaction. The reaction mixture is poured into ice-water and extracted with three 3 ml portions of ether. The ethereal solution is washed three times with water and concentrated by evaporation. The solid residue is separated into the two isomers by chromatography through a column of silica gel (elution with a 95:5 mixture of methylene chloride/methanol), affording 35.8 mg of product with a melting point of 136°–139° C. and 26.6 g of product with a melting point of 122°–126° C.

$^1$H-NMR (250 mHz; CDCl$_3$, TMS): 4.85 (s) (—CH$_2$-imidazole); 7.04; 7.12; 7.72; 8.02 (4 s) (imidazole ring protons); 3.26 (narrow multiplet) (C$_2$—H); mass spectrum m/e: 678 (M+, C$_{39}$H$_{54}$N$_2$O$_8$). The structural assignment to the 4-methyl and 5-methyl derivative of the two isomers cannot be made with certainty.

33. Preparation of 5-O-imidazol-1'-ylacetylmilbemycin D (compound 2.4)

Following the procedure of Example 32, 5-O-(imidazol-1'-yl)acetylmilbemycin D with a melting point of 108°–112° C. is prepared by reacting 5-O-chloroacetylmilbemycin D with imidazole.

$^1$H-NMR (250 mHz; CDCl$_3$, TMS); 4.90 (s) —CH$_2$-imidazole; 3.25 (m) (C$_2$—H).

34. Preparation of 5-O-(1,2,4-triazol-1'-yl)acetylmilbemycin A$_4$ (R=C$_2$H$_5$) (compound 1.1)

390 mg of dicyclohexylcarbodiimide are added to a solution of 500 mg of milbemycin A$_4$ and 400 mg of 1,2,4-triazol-1-ylacetic acid in 20 ml of absolute tetrahydrofuran and the mixture is stirred for 2 hours at 20°–25° C. Then 5 ml of pyridine are added and the mixture is stirred for another 15 hours. The reaction mixture is then poured into ice-water and 1N hydrochloric is added until the onset of weakly acid reaction. The reaction product is extracted with ether and undissolved solid is removed by filtration. The ethereal solution is dried and concentrated by evaporation to give a crude product which crystallises upon treatment with hexane. Yield: 650 mg of pale yellowish crystals with a melting point of 80°–85° C.

$^1$H-NMR (250 mHz; CDCl$_3$, TMS): 5.05 (s) (—CH$_2$-triazole); 8.0 and 8.25 (2 s) (triazole ring protons); 3.25 (narrow multiplet) (C$_2$—H).

35. Preparation of 5-O-(1,2,4-triazol-1'yl)acetylmilbemycin D copper(II) complex (compound 2.1 g)

A solution of 12.7 mg of copper(II) chloride in 0.5 ml of ethanol is added to a solution of 100 mg of 5-O-(1,2,4-triazol-1'-yl)milbemycin D in 0.75 ml of absolute ethanol. After a short time, bluish green crystals precipitate from the initially clear green solution. Yield: 85 mg of the title compound with a melting point of 178° C. (dec).

36. Preparation of 5-O-(1,2,4-triazol-1'-yl)acetyl-13β-chloromilbemycin D (compound 2.10)

Following the procedure of Example 34, 141 mg of the title compound are obtained from 150 mg of 13β-chloromilbemycin D and 81 mg of 1,2,4-triazol-1-ylacetic acid.

$^1$H-NMR (250 mg, CDCl$_3$): 3.07 (bd, J=9) (C$_{25}$H); 4.09 (d, J=10) (C$_{13}$H); 5.07 (s) (CH$_2$-triazole); 7.98 and 8.24 (2s) (triazole ring protons).

37. Preparation of 5-O-(1,2,4-triazol-1'-yl)acetyl-13β-chloromilbemycin D, copper (II) complex (compound 2.2b)

Following the procedure of Example 35, 29 mg of the title compound are obtained from 44 mg of 5-O-(1,2,4-triazol-1'-yl)acetyl-13β-chloromilbemycin D and 75 mg of copper(II) chloride.2H$_2$O.

38. Preparation of 5-O-(1,2,4-triazol-1'-yl)acetyl-13β-chloromilbemycin D, zinc (II) complex (compound 2.2a)

A solution of 5 mg of zinc(II) chloride in 0.25 ml of ethanol is added to a solution of 37 mg of 5-O-(1,2,4-triazol-1'-yl)acetyl-13β-cholormilbemycin D in 0.50 ml of ethanol. Crystals begin to precipitate upon addition of 0.50 ml of water. Yield: 38 mg of the title compound.

$^1$H-NMR (250 MHz, CDCl$_3$): 3.07 (bd, J=9) (C$_{25}$H); 4.09 (d, J=11), (C$_{13}$H); 5.10 (s) (CH$_2$-triazole); 8.08 and 8.48 (2 bs) (triazole ring protons).

39. Preparation of 5-O-(1,2,4-triazole-1'-yl)acetyl-13β-chloromilbemycin A$_4$ (compound 1.9)

Following the procedure of Example 34, 159 mg of the title compound are obtained from 150 mg of 13-β-chloromilbemycin A$_4$ and 83 mg of 1,2,4-triazol-1-ylacetic acid.

$^1$H-NMR (25 MHz, CDCl$_3$): 3.06 (dt, J$_d$=3, J$_t$=10 (C$_{25}$H); 4.09 (d, J=10) (C$_{13}$H); 5.07 (s) (CH$_2$-triazole); 7.98 and 8.24 (2s) (triazole ring protons).

40. Preparation of 5-O-(1,2,4-triazol-1'-yl)acetyl-13β-chloromilbemycin A$_4$, iron(II) complex (compound 1.1c)

0.50 ml of a solution of 174 mg of iron(II) chloride.4-H$_2$O in 10 ml of a 9:1 mixture of ethanol/water are added to a solution of 30 mg of 5-O-(1,2,4-triazol-1'-yl)acetyl-13β-chloromilbemycin A$_4$ in 3 ml of a 2:1 mixture of benzene/methanol. The mixture is allowed to stand for a short time and then concentrated by evaporation. The residue is taken up in a small amount of benzene and lyophilised, affording 37 mg of the title compound in the form of a yellowish brown powder 41. Preparation of 5-O-(1,2,4-triazol-1'-yl)acetyl-13β-chloromilbemycin A$_4$, copper(II) complex (compound 1.1d)

86 mg of anhydrous copper(II) chloride in 10 ml of ethanol are added to a solution of 40 mg of 5-O-(1,2,4-triazol-1'-yl)acetyl-13β-chloromilbemycin A$_4$ in 0.50 ml of ethanol. The mixture is allowed to stand for a short time and then concentrated by evaporation. The residue is taken up in 5 ml of benzene and lyophilised, affording 44 mg of the title compound in the form of a greenish powder.

42. Preparation of 5-O-(1,2,4-triazol-1'-yl)acetyl-13β-chloromilbemycin A$_4$, zinc(II) complex (compound 1.1a)

0.50 ml of a solution of 86 mg of zinc(II) chloride in 10 ml of ethanol are added to a solution of 39 mg of 5-O-(1,2,4-triazol-1'-yl)acetyl-13β-chloromilbemycin A$_4$ in 0.50 ml of ethanol. The reaction mixture is then concentrated by evaporation and the residue is taken up in 3 ml of benzene and lyophilised, affording 43 mg of the title compound in the form of a colourless powder.

$^1$H-NMR (250, CDCl$_3$): 3.07 (dt, J$_d$=3, J$_t$=10) (C$_{25}$H); 4.09 (d, J−10) (C$_{13}$H); 5.19 (6S) (CH$_2$-triazole); 8.28 and 9.02 (2bs) (triazole ring protons)

Further compounds of this invention can be prepared in accordance with the above Examples or by one of the initially described methods.

Milbemycin A$_4$ series:
No.
1.2 5-O-(imidazol-1'-yl)acetylmilbemycin A$_4$,
1.3 5-O-(pyrazol-1'-yl)acetylmilbemycin A$_4$,
1.4 5-O-(2'-methylimidazol-1'-yl)acetylmilbemycin A$_4$,
1.5 5-O-(tetrazol-1'-yl)acetylmilbemycin A$_4$,
1.6 5-O-(imidazol-1'-yl)acetyl-13β-fluoromilbemycin A$_4$,
1.7 5-O-(imidazol-1'-yl)acetyl-13β-chloromilbemycin A$_4$,
1.8 5-O-(2'-ethylimidazol-1'-yl)acetyl-13β-chloromilbemycin A$_4$,
1.9 5-O-(1,2,4-triazol-1'-yl)acetyl-13β-chloromilbemycin A$_4$,
1.10 5-O-(pyrazol-1'-yl)acetyl-13β-chloromilbemycin A$_4$,
1.11 5-O-(1,2,4-triazol-1'-yl)acetyl-13β-flUoromilbemycin A$_4$,
1.12 5-O-(4'(5')methylimidazol-1'-yl)acetyl-13β-bromomilbemycin A$_4$,
1.13 5-O-(1,2,4-triazol-4'-yl)acetyl-13β-chloromilbemycin A$_4$,
1.14 5-O-(imidazol-1'-yl)acetyl-13β-iodomilbemycin A$_4$,
1.15 5-O-(1,2,3-triazol-1'-yl)acetyl-13β-chloromilbemycin A$_4$,
1.16 5-O-(1,2,4-triazol-1'-yl)acetyl-13β-bromomilbemycin A$_4$,
1.17 5-O-(1,2,4-triazol-1'-yl)acetyl-13β-iodomilbemycin A$_4$,
1.18 5-O-(pyrazol-1'-yl)acetyl-13β-iodomilbemycin A$_4$, Milbemycin D series:
No.
2.5 5-O-(2'-methylimidazol-1'-yl)acetylmilbemycin D,
2.6 5-O -(tetrazol-1'-yl)acetylmilbemycin D,
2.7 5-O-(pyrazol-1'-yl)acetylmilbemycin D,
2.8 5-O-(1,2,3-triazol-1'-yl)acetylmilbemycin D,
2.9 5-O-(1,2,4-triazol-1'-yl)acetyl-13β-fluoromilbemycin D,
2.10 5-O-(1,2,4-triazol-1'-yl)acetyl-13β-chloromilbemycin D,
2.11 5-O-(imidazol-1'-yl)acetyl-13β-chloromilbemycin D,
2.12 5-O-(2'-ethylimidazol-1'-yl)acetyl-13β-chloromilbemycin D,
2.13 5-O-(pyrazol-1'-yl)acetyl-13β-fluoromilbemycin D,
2.14 5-O-(pyrazol-1'-yl)acetyl-13β-chloromilbemycin D,
2.15 5-O-[4'(5')-methylimidazol-1'-yl]-13β-chloromilbemycin D,
2.16 5-O-(tetrazol-1'-yl)acetyl-13β-fluoromilbemycin D,
2.17 5-O-(1,24-triazol-4'-yl)acetyl-13β-fluoromilbemycin D,
2.18 5-O-(1,2,4-triazol-4'-yl)acetyl-13β-chloromilbemycin D,
2.19 5-O-(1,2,3-triazol-1'-yl)acetyl-13β-fluoromilbemycin D,
2.20 5-O-(1,2,3-triazol-1'-yl)acetyl- 13β-chloromilbemycin D,
2.21 5-O-(imidazol-1'-yl)acetyl-13β-fluoromilbemycin D,
2.22 5-O-(1,2,4-triazol-1'-yl)acetyl-13β-bromomilbemycin D,
2.23 5-O-(1,2,4-triazol-1'-yl)acetyl-13β-iodomilbemycin D,
2.24 5-O-(2-ethyl-4-methylimidazol-1'-yl)acetylmilbemycin D.

Milbemycin A$_3$ series:
3.1 5-O-(pyrazol-1'-yl)acetylmilbemycin A$_3$,
3.2 5-O-(1,2,4-triazol-1'-yl)acetylmilbemycin A$_3$,
3.3 5-O-(1,2,4-triazol-4'-yl)acetylmilbemycin A$_3$,
3.4 5-O-(imidazol-1'yl)acetylmilbemcin A$_3$,
3.5 5-O-(pyrazol-1'-yl)acetyl-13β-chloromilbemycin A$_3$,
3.6 5-O-(1,2,4-triazol-1'-yl)acetyl-13β-chloromilbemycin A$_3$,
3.7 5-O-(imidazol-1'-yl)acetyl-13β-chloromilbemycin A$_3$, 13-Deoxy-22,23-dihydroavermectin-Bla-aglycon series:
4.1 5-O-(pyrazol-1'-yl)acetyl-13-deoxy-22,23-dihydroavermectin-Bla-aglycon,
4.2 5-O-(1,2,3-triazol-1'-yl)acetyl-13-deoxy-22,23-dihydroavermectin-Bla-aglycon,
4.3 5-O-(1,2,4-triazol-1'-yl)acetyl-13-deoxy-22,23-dihydroavermectin-Bla-aglycon, 4.4  5-O-(tetrazol-1'-yl)acetyl-13-deoxy-22,23-dihydroavermectin-B1a-aglycon,
4.5  5-O-[4'(5')isopropylimidazol-1'-yl)acetyl-13-deoxy-22,23-dihydroavermectin-B1a-aglycon,
4.6  5-O-(imidazol-1'-yl)acetyl-13-deoxy-22,23-dihydroavermectin-B1a-aglycon,
4.7  5-O-(pyrazol-1'-yl)acetyl-13β-chloro-13-deoxy-22,23-dihydroavermectin-B1a-aglycon,
4.8  5-O-(1,2,3-triazol-1'-yl)acetyl-13β-chloro-13-deoxy-22,23-dihydroavermectin-B1a-aglycon,
4.9  5-O-(1,2,4-triazol-1'-yl)acetyl-13β-chloro-13-deoxy-22,23-dihydroavermectin-B1a-aglycon,
4.10  5-O-(tetrazol-1'-yl)acetyl-13β-chloro-13-deoxy-22,23-dihydroavermectin-B1a-aglycon,
4.11  5-O-(imidazol-1'-yl)acetyl-13β-chloro-13-deoxy-22,23-dihydroavermectin-B1a-aglycon,
4.12  5-O-(1,2,4-triazol-1'-yl)acetyl-13β-fluoro-13-deoxy-22,23-dihydroavermectin-B1a-aglycon,
4.13  5-O-(2'-imidazol-1'-yl)acetyl-13β-chloro-13-deoxy-22,23-dihydroavermectin-B1a-aglycon.

Following the procedure of Example 9, metal complexes can be prepared from the above compounds, e.g.:

| Complex salts of 5-0-(1,2,4-triazol-1'-yl)acetylmilbemycin D | | | |
|---|---|---|---|
| 2.1a | zinc complex | (.½ ZnCl$_2$) | m.p. 183° C. (dec.) |
| 2.1b | manganse complex | (.½ MnCl$_2$) | |
| 2.1c | nickel complex | (.½ NiCl$_2$) | |
| 2.1d | cobalt complex | (.½ CoCl$_2$) | |
| 2.1e | cadmium complex | (.½ CdSO$_4$) | |
| 2.1f | iron complex | (.½ FeSO$_4$) | |
| 2.1g | copper complex | (.½ CuCl$_2$) | m.p. 178° C. (dec.) |
| Complex salts of 5-0-(1,2,4-triazol-1'-yl)-13β-chloromilbemycin D | | | |
| 2.2a | zinc complex | (.½ ZnCl$_2$) | m.p. 182° C. (dec.) |
| 2.2b | copper complex | (.½ CuCl$_2$) | m.p. 174° C. (dec.) |
| Complex salts of 5-0-(1,2,4-triazol-1'-yl)acetyl-13β-chloro-milbemycin A$_4$ | | | |
| 1.1a | zinc complex | (.½ ZnCl$_2$) | m.p. 176° C. (dec.) |
| 1.1b | manganese complex | [.½ Mn(NO$_3$)$_2$] | m.p. 183° C. (dec.) |
| 1.1c | iron complex | (.½ FeCl$_2$) | m.p. 181° C. (dec.) |
| 1.1d | copper complex | (.½ CuCl$_2$) | m.p. 179° C. (dec.) |

The above milbemycin derivatives of formula I can be purified via their salts (by treatment with the appropriate acid) and sold or used in this form. Suitable salts are e.g. the hydrochlorides, sulfates, nitrates, tosylates, tartrates or oxalates.

FORMULATION EXAMPLES FOR ACTIVE INGREDIENTS OF FORMULA I (throughout, percentages are by weight)

| Wettable powders | (a) | (b) | (c) |
|---|---|---|---|
| compound Z1-Z55 or 1.1-4.13 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

Emulsifiable concentrate
compound of Z1-Z55 or 1.1-4.13: 10%,
octylphenol polyethylene glycol ether (4-5 moles of ethylene oxide): 3%,
calcium dodecylbenzenesulfonate: 3%,
castor oil polygycol ether (36 moles of ethylene oxide): 4%,
cyclohexanone: 30%,
xylene mixture: 50%.

Emulsions of any required concentration can be obtained from this concentrate by dilution with water.

| Dusts | (a) | (b) |
|---|---|---|
| compound of Z1-Z55 or 1.1-4.13 | 5% | 8% |
| talcum | 95% | — |
| kaolin | — | 92% |

Ready for use dusts are obtained by mixing the active ingredient with the carrier, and grinding the mixture in a suitable mill.

Extruder granulate
compound of Z1-Z55 or 1.1-4.13: 10%,
sodium lignosulfonate: 2%,
carboxymethylcellulose: 1%,
kaolin: 87%.

The active ingredient is mixed and ground with the adjuvants, and the mixture is subsequently moistened with water. The mixture is extruded and then dried in a stream of air.

Tablets and bolusses
I
compound Z1-Z55 or 1.1-4.13: 33.0%,
methyl cellulose: 0.80%,
highly dispersed silic acid: 0.80%,
maize starch: 8.40%.

The methyl cellulose is stirred in water and allowed to swell. The silic acid is stirred in to give a homogeneous suspension. The active ingredient and maize starch are mixed. The aqueous suspension is blended with this mixture, which is kneaded to a paste. The paste is granulated through a sieve (mesh size 12M) and then dried.
II
lactose (cryst.): 22.50%,
maize starch: 17.00%,
microcrystalline cellulose: 16.50%,
magnesium stearate: 1.00%.
All four ingredients are thoroughly mixed.
III Phases I and II are mixed and compressed to tablets or bolusses.

If the compounds of formula I or V, or compositions containing them, are used for controlling endoparasitic nematodes in domestic animals and productive livestock, for example cattle, sheep, goats, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, boluses or capsules.

If the physical and toxicological properties of solutions or emulsions permit it, the compounds of formula I or V, or compositions containing them, can also be injected into animals for example subcutaneously, or applied to the bodies of the animals by the pour-on method. Administration by means of salt licks or molasses blocks is also possible.

Biological Examples

B1: Insecticidal stomach poison action against *Spodoptera littoralis*

Potted cotton plants in the 5-leaf stage are sprayed with a solution containing 3, 12.5 or 50 ppm of the test compound in acetone/water. After the coating has dried, the plants are populated with about 30 larvae ($L_1$ stage) of *Spodoptera littoralis*. Two plants are used for each test compound and test species. The test is carried out at about 24° C. and 60% relative humidity. Evaluations and intermediate evaluations of moribund insects, larval growth and feeding damage are made after 24, 48 and 72 hours. Complete kill was achieved after 24 hours with the compounds of formulae I and V, e.g. compounds Z1, Z8, 1.1, 2.1 g, 2.1a or 1.1c at a concentration of 3 ppm.

B2: Action against plant-destructive acarids: OP-sensitive *Tetranychus urticae*

16 hours before the start of the test, the primary leaves of bean plants (*Phaseolus vulgaris*) are infected with an infested piece of leaf from a mass culture of *Tetranychus urticae*. Upon removal of the piece of leaf, the plants infested with all stages of the mites are sprayed to drip point with a solution containing 1.6 ppm of the test compound. The temperature in the greenhouse compartment is about 25° C.

The percentage of mobile stages (adults and nymphs) and of eggs is evaluated under a stereoscopic microscope after 7 days. Compounds of formula I and V, e.g. Z1, Z3, Z7, Z8 or Z10, effected complete kill at a concentration of 0.4 ppm.

B3: Action against $L_1$ larvae of *Lucilia sericata*

1 ml of an aqueous suspension of test compound is mixed with 3 ml of a special larval culture medium at about 50° C. such that a homogeneous composition containing 250 ppm or 125 ppm is obtained. About 30 *Lucilia sericata* larvae ($L_1$) are put into each test tube containing active ingredient. A mortality count is made after 4 days. All compounds of formulae I and V listed with their physical data effected 100% kill at a concentration of 250 ppm.

B4: Acaricidal action against *Boophilus microplus* (Biarra strain)

Adhesive tape is applied vertically across a PVC plate so that 10 fully replete female *Boophilus microplus* ticks (Biarra strain) can be affixed thereto with their backs, side by side, in a row. Each tick is injected from an injection needle with 1 $\mu$l of a liquid which contains a 1:1 mixture of polyethylene glycol and acetone, in which mixture a specific amount of test compound of 5, 0.5 or 0.05 $\mu$g per tick is dissolved. Control ticks are injected with liquid containing no test compound. After this treatment, the ticks are detached from the support and kept in an insectarium at about 28° C. and 80% relative humidity until oviposition has taken place and the larvae have hatched from the eggs of the control ticks. The activity of the test compound is determined with the $IR_{90}$, i.e. the effective dose is determined at which 9 out of 10 female ticks (90%) even after 30 days lay eggs from which larvae are unable to hatch.

Compounds of formulae I and V, e.g. Z1, Z3, Z7, Z8, Z10, 2.1, 2.2 to 2.3, 2.4, 2.1g, 2.1a, 1.9, 2.10, 1.1a, 1.1c or 1.1d achieved an $IR_{90}$ of 0.5 $\mu$g.

B5: Trial with sheep infected with nematodes (*Haemonchus concortus* and *Trichostrongylus colubriformis*)

The test compound is administered in the form of a suspension with a stomach probe or by intraruminal injection to sheep which have been artificially infected with *Haemonchus concortus* and Trichostrongylus. Three animals are used for each dose. Each sheep is treated only once with a single dose of 1 mg or 0.5 mg/kg of body weight. Evaluation is made after 7 days by comparing the number of worm eggs excreted in the faeces of the sheep before and after treatment.

Untreated sheep infected simultaneously and in the same manner are used as controls. In comparison with untreated and infected control groups, there is no nematode infestation (=complete reduction of the number of worm eggs in the faeces) in sheep which have been treated with one of the compounds of formula I or V listed with physical data at a concentration of 1 mg/kg.

B6: Contact action against *Aphis craccivora*

Pea plantlets infected with all development stages of the aphid are sprayed with a solution of the test compound prepared from an emulsifiable concentrate and containing 50 ppm, 25 ppm or 12.5 ppm of active ingredient. After 3 days a count is made of more than 80% dead aphids or aphids that have dropped from the plants. Only at this degree of activity is a composition rated as effective.

Complete kill (=100%) was effected with compounds of formula I and e.g. compounds Z1, Z7, Z8, 1.1 or 1c at a concentration of 12.5 ppm.

B7: Larvicidal action against *Aedes aegypti*

A 1% solution of the test compound in acetone is pipetted onto the surface of 150 ml of water in beakers in amounts sufficient to give concentrations of 10 ppm, 3.3 ppm and 1.6 ppm. After the acetone has evaporated, about 30–40 three-day-old Aedes larvae are put into each beaker and a mortality count is made after 1, 2 and 5 days.

Compounds of formulae I and V, e.g. Z1, 2.1, 1.1, 2.1a or 1.1d, effected in this test a complete kill of all larvae at a concentration of 1.6 ppm after 1 day.

What is claimed is:

1. A milbemycin derivative of the formula I

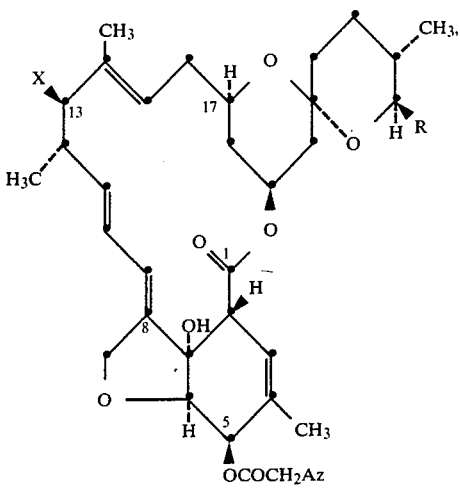

wherein X is hydrogen or β-halogen, R is methyl, ethyl, isopropyl or sec-butyl and Az is a 5 membered heterocyclic aromatic ring which contains 2–4 nitrogen atoms and is attached in the 1-position and which is unsubstituted or substituted by one or two $C_1$–$C_6$alkyl groups, or an acid addition salt or metal complex thereof.

2. A compound of the formula I according to claim 1, wherein R is isopropyl and X and Az are as defined in claim 1.

3. A compound of the formula I according to claim 1, wherein Az is imidazole, pyrazole, 1,2,3-triazole, 1,2,4-triazole, tetrazole, 2-ethyl-4-methylimidazole, 2-isopropylimidazole, methylimidazole, 3,5-dimethyltriazole, ethyltriazole or 3,4-diethyltriazole, each of which is attached in the 1-position.

4. A compound of the formula I according to claim 3, wherein X is hydrogen or β-chlorine, R is ethyl or isopropyl, and Az is 1,2,4-triazol-1-yl.

5. 5-O-(1,2,4-Triazol-1'-yl)acetyl-13-βchloromilbemycin D, or a salt or metal complex thereof.

6. A metal complex according to claim 5 with a metal selected from the group consisting of copper, zinc, manganese, chromium, iron, nickel, cobalt and molybdenum.

7. A pesticidal composition containing at least one compound according to claim 1 together with a suitable carrier therefor.

8. A pesticidal composition according to claim 7, which contains a compound according to claim 2.

9. A pesticidal composition according to claim 7, which contains a compound according to claim 3.

10. A pesticidal composition according to claim 7, which contains a compound according to claim 4.

11. A pesticidal composition according to claim 7, which contains a compound according to claim 5.

12. A pesticidal composition according to claim 7, which contains a compound according to claim 6.

13. A method of controlling insects and pests of the order Acarina at a locus, which comprises applying to said locus a pesticidally effective amount of a compound according to claim 1.

14. A method according to claim 13 of controlling nematodes at a locus, which comprises applying to said locus a nematicidally effective amount of a compound according to claim 1.

15. A method of controlling ecto- and endoparasites on or in warm-blooded animals, which comprises applying or administering to said animals a pesticidally effective amount of a compound according to claim 1.

16. A method of controlling pests which are parasites of animals or plants, which comprises applying to said animals or plants a pesticidally effective amount of a compound according to claim 1.

* * * * *